(12) United States Patent
Trocme-Thibierge et al.

(10) Patent No.: US 8,940,785 B2
(45) Date of Patent: Jan. 27, 2015

(54) ASSOCIATION BETWEEN 4-{3-[CIS-HEXAHYDROCYCLOPENTA[C]PYRROL-2(1H)-YL]PROPOXY}BENZAMIDE AND AN ACETYLCHOLINESTERASE INHIBITOR, AND PHARMACEUTICAL COMPOSITIONS CONTAINING IT

(75) Inventors: Caryn Trocme-Thibierge, Bois Colombes (FR); Aurore Sors, Paris (FR); Florence Keime-Guibert, Singapore (SG)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 13/461,063

(22) Filed: May 1, 2012

(65) Prior Publication Data

US 2012/0283244 A1 Nov. 8, 2012

(30) Foreign Application Priority Data

May 2, 2011 (FR) ...................... 11 01347

(51) Int. Cl.
*A01N 43/38* (2006.01)
*A61K 31/40* (2006.01)
*A01N 43/00* (2006.01)
*A01N 43/46* (2006.01)
*A61K 31/55* (2006.01)

(52) U.S. Cl.
USPC .......................................... 514/412; 514/215

(58) Field of Classification Search
USPC ....................................................... 514/412
See application file for complete search history.

(56) References Cited

FOREIGN PATENT DOCUMENTS

WO WO 2005/089747 11/2005
WO WO 2010043787 A1 * 4/2010

OTHER PUBLICATIONS

Ringman et al. (Treatment of REM sleep behavior disorder with donepezil: a report of three cases. Neurology 2000; 55: 870-1).*
Bembenek, et al., Bioorganic and Medicinal Chemistry, vol. 16, No. 6, p. 2968-2973, Dec. 25, 2007.
Berlin M., et al, Expert Opinion on Therapeutic Targets, vol. 17, No. 6, p. 675-687, Jun. 1, 2007.
Celerier Aurelie, et al., Learning and Memory, vol. 11, No. 2, p. 196-204. Mar. 2004.
French Preliminary Search Report for FR1101347 of Aug. 11, 2011.

* cited by examiner

*Primary Examiner* — Layla Soroush
(74) *Attorney, Agent, or Firm* — Hueschen and Sage

(57) ABSTRACT

Association between 4-{3-[cis-hexahydrocyclopenta[c]pyrrol-2(1H)-yl]propoxy}benzamide of formula (I):

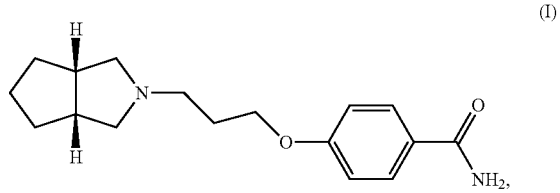

or an addition salt thereof with a pharmaceutically acceptable acid or base, and an acetylcholinesterase inhibitor.
Medicinal products containing the same which are useful in the treatment of cognitive disturbances associated with cerebral ageing and with neurodegenerative diseases.

7 Claims, 5 Drawing Sheets

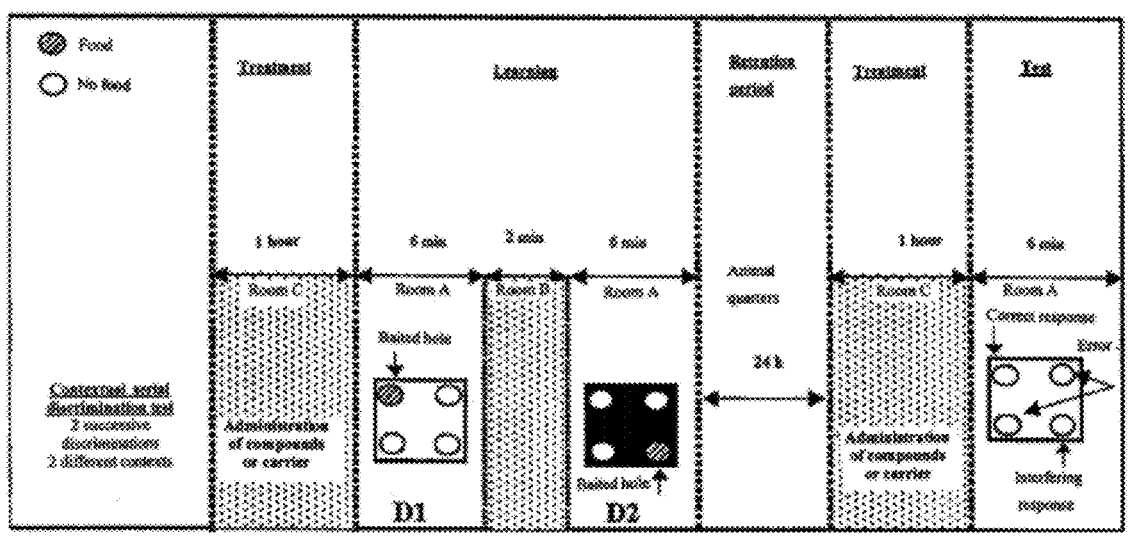
Figure 1. Experiment procedure.
(modified, after Trouche *et al.*, 2010)

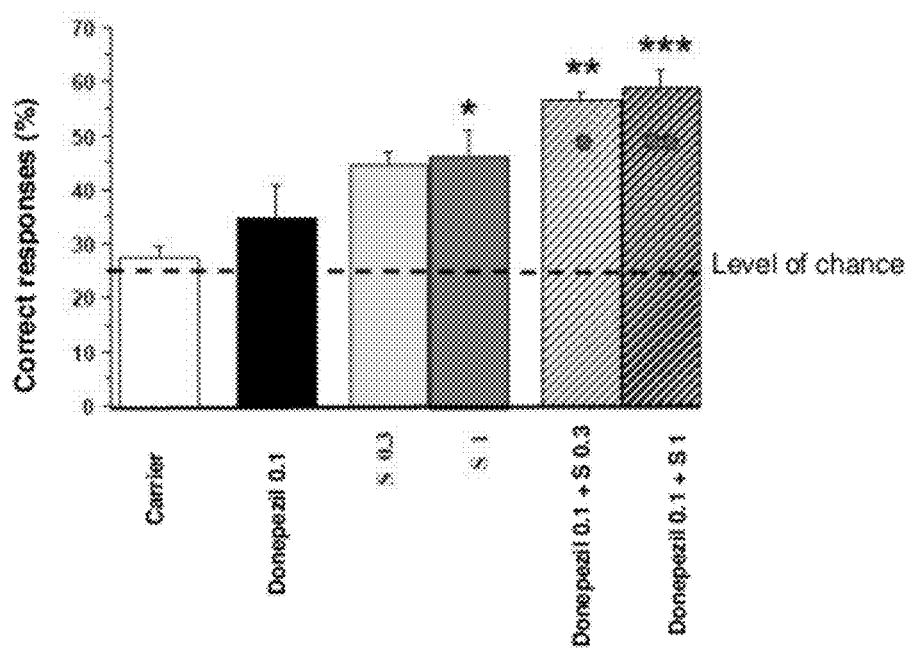

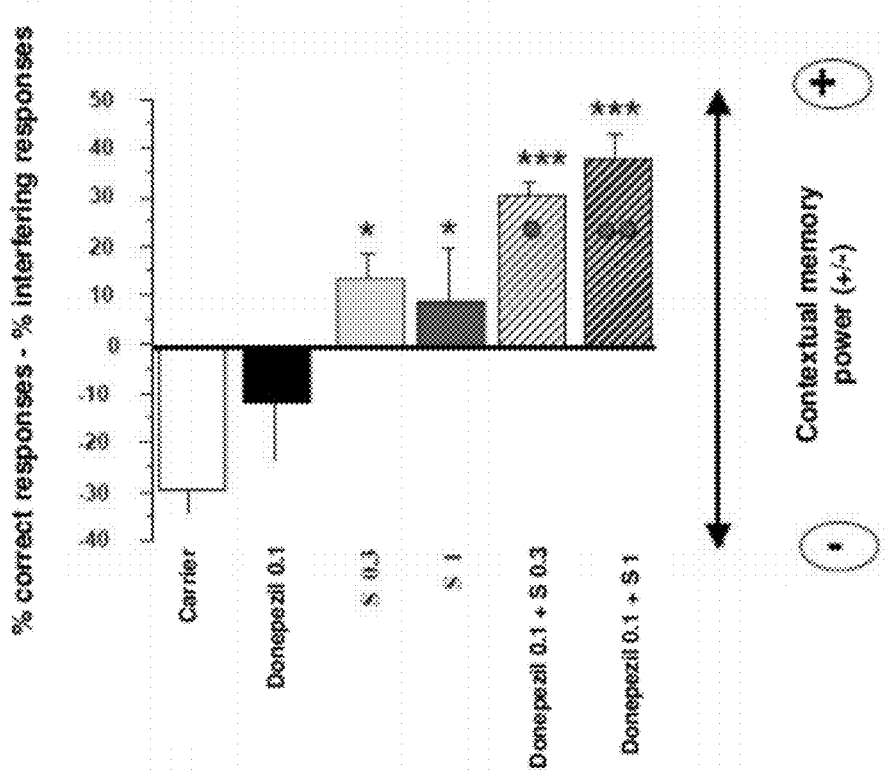

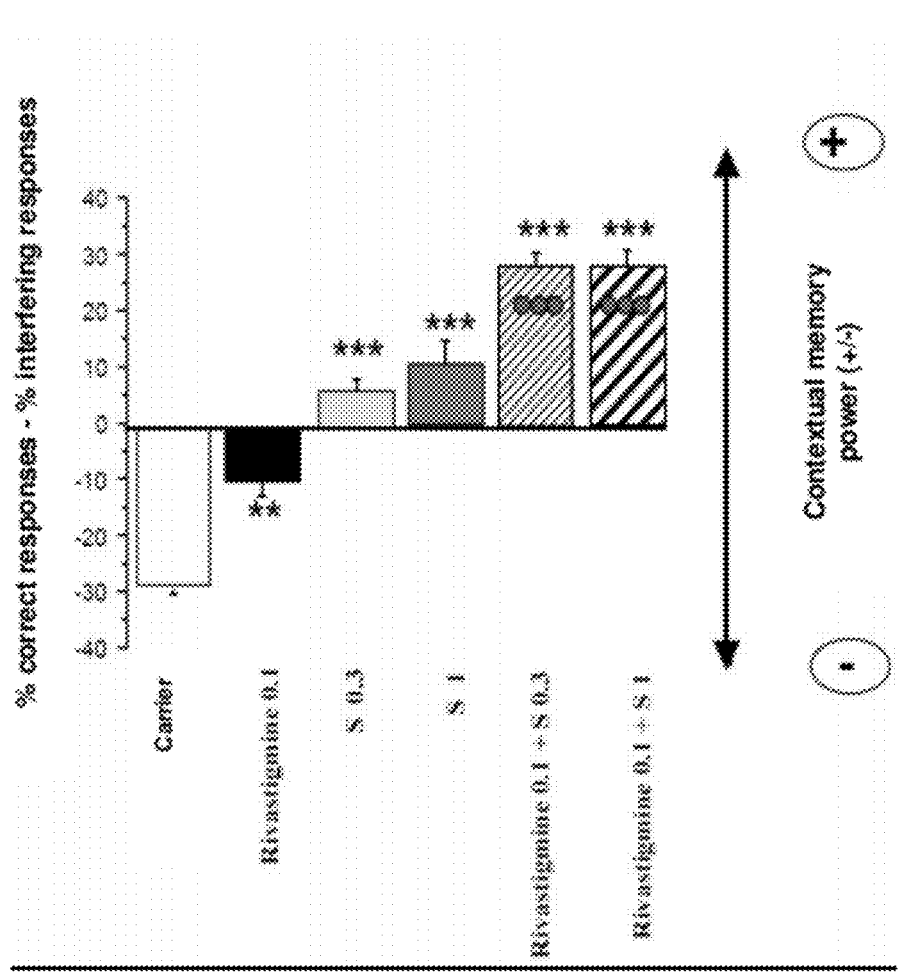

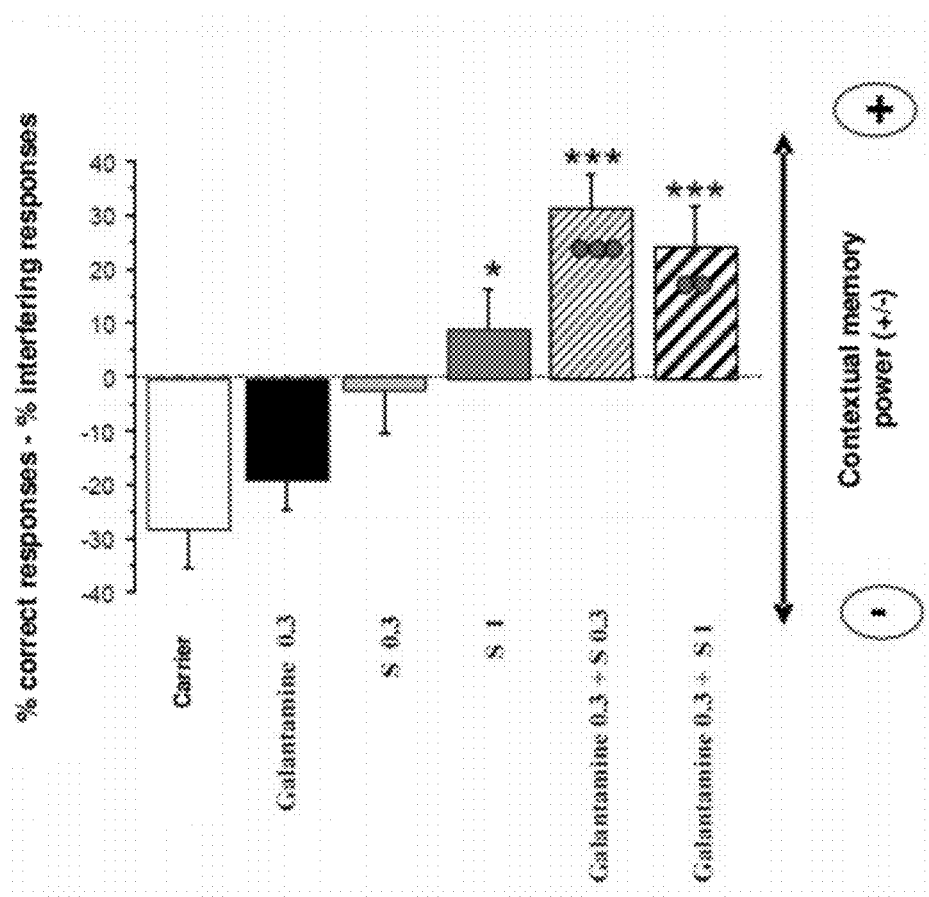

ASSOCIATION BETWEEN 4-{3-[CIS-HEXAHYDROCYCLOPENTA[C]PYRROL-2(1H)-YL]PROPOXY}BENZAMIDE AND AN ACETYLCHOLINESTERASE INHIBITOR, AND PHARMACEUTICAL COMPOSITIONS CONTAINING IT

The present invention relates to a new association between 4-{3-[cis-hexahydrocyclopenta[c]pyrrol-2(1H)-yl]propoxy}benzamide of formula (I):

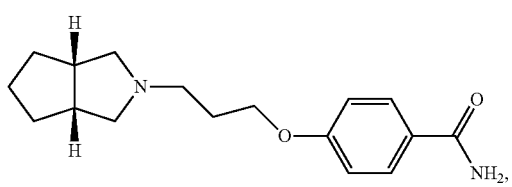

or an addition salt thereof with a pharmaceutically acceptable acid or base, and an acetylcholinesterase inhibitor, for obtaining pharmaceutical compositions for use in the treatment of cognitive disturbances associated with cerebral ageing and with neurodegenerative diseases.

4-{3-[cis-Hexahydrocyclopenta[c]pyrrol-2(1H)-yl]propoxy}benzamide has the characteristic of interacting with central histaminergic systems in vivo. These properties provide it with activity in the central nervous system and, more especially, in the treatment of cognitive deficiencies associated with cerebral ageing and with neurodegenerative diseases.

4-{3-[cis-Hexahydrocyclopenta[c]pyrrol-2(1H)-yl]propoxy}benzamide, its preparation and its therapeutic use have been described in Patent Application WO2005/089747.

The Applicant has now found that 4-{3-[cis-hexahydrocyclopenta[c]pyrrol-2(1H)-yl]propoxy}-benzamide of formula (I), or an addition salt thereof with a pharmaceutically acceptable acid or base, used in association with an acetylcholinesterase inhibitor has valuable properties for the treatment of cognitive disturbances associated with cerebral ageing and with neurodegenerative diseases.

Neurodegenerative diseases related to cerebral ageing such as Alzheimer's disease are characterised by disturbances of memory and cognitive dysfunction. The cognitive disturbances are usually associated with a reduction in the ability of neurons to synthesise and release certain neurotransmitters. There is moreover observed a progressive loss of synaptic plasticity and of neuronal processes, this neuronal loss being accelerated in certain specific regions of the brain. Among the various neurotransmitters, central histamine and acetylcholine play a crucial part in the control of cognitive functions (Witkin and Nelson, *Pharmacol. & Therap.*, 2004, 103, 1-20) and their levels have been shown to greatly diminish in patients suffering from Alzheimer's disease compared to those observed in healthy elderly people (Panula et al., *Neuroscience*, 1998, 82(4), 993-997).

Type $H_3$ histaminergic receptors, which are especially abundant in the central nervous system, are mainly presynaptic modulators of neural transmission and are present in a variety of neuronal circuits relevant to cognition (Blandina et al., *Learn Mem.*, 2004, 11(1), 1-8). They act by negatively regulating the release of neurotransmitters such as histamine, acetylcholine, serotonin, noradrenaline and dopamine. Given that histaminergic neurons seem to be largely spared in Alzheimer's disease, compounds that are antagonists or inverse agonists of $H_3$ receptors could open the way to new treatments for the cognitive disturbances related to cerebral ageing. Conversely, progressive degeneration of cholinergic neurons is observed in the course of Alzheimer's disease. Acetylcholinesterase inhibitors such as donepezil are commonly used in the symptomatic treatment of Alzheimer's disease in order to limit the lowering of acetylcholine levels in the brain by blocking the action of acetylcholinesterase. It has been shown that acetylcholinesterase inhibitors, like antagonists/inverse agonists of $H_3$ receptors, make it possible to improve cognitive properties in various animal models of episodic memory and working memory (Esbenshade et al., *Br. J. Pharmacol.*, 2008, 154(6), 1166-1181; Yuede et al., *Behav. Pharmacol.*, 2007, 18(5-6), 347-363). Improving cognitive functions may therefore be based on two types of strategy targeting either histamine or acetylcholine.

The present invention has shown, surprisingly, that the effects of acetylcholinesterase inhibitors are potentiated by those of 4-{3-[cis-hexahydrocyclopenta[c]pyrrol-2 (1H)-yl]propoxy}-benzamide or addition salts thereof with a pharmaceutically acceptable acid or base. Accordingly, co-administration of these compounds could make it possible to improve the cognitive performance of patients compared to the simple administration of an acetylcholinesterase inhibitor without, however, increasing the adverse effects associated with the treatment (especially gastrointestinal disturbances such as nausea or diarrhoea, headaches or fatigue). In other words, treatments involving therapeutic doses of acetylcholinesterase inhibitor that are lower than those customarily used in mono-therapy can therefore now be envisaged, with equivalent or even superior cognitive performance and fewer adverse effects.

This unforeseeable effect makes it possible to envisage using associations between 4-{3-[cis-hexahydrocyclopenta[c]pyrrol-2(1H)-yl]propoxy}benzamide, or an addition salt thereof, and an acetylcholinesterase inhibitor in the treatment of cognitive disturbances associated with cerebral ageing and with neurodegenerative diseases. The cognitive disturbances associated with Alzheimer's disease and with Parkinson's disease are being especially targeted.

4-{3-[cis-Hexahydrocyclopenta[c]pyrrol-2(1H)-yl]propoxy}benzamide is used preferably in the form of an oxalate or hydrochloride within the context of the invention.

Among the acetylcholinesterase inhibitors according to the invention, donepezil, rivastigmine and galantamine are especially preferred. Preferably, donepezil is used in the form of a hydrochloride, rivastigmine in the form of a hydrogen tartrate, and galantamine in the form of a hydrobromide.

More especially, the association of 4-{3-[cis-hexahydrocyclopenta[c]pyrrol-2(1H)-yl]propoxy}-benzamide and donepezil is used in the treatment of cognitive disturbances associated with Alzheimer's disease, whereas the association of 4-{3-[cis-hexahydrocyclopenta[c]pyrrol-2(1H)-yl]propoxy}benzamide and rivastigmine is preferred in the treatment of cognitive disturbances associated with Parkinson's disease.

The invention accordingly relates to use of the association between 4-{3-[cis-hexahydrocyclopenta[c]pyrrol-2(1H)-yl]propoxy}benzamide, or addition salts thereof with a pharmaceutically acceptable acid or base, and an acetylcholinesterase inhibitor in obtaining pharmaceutical compositions intended for the treatment of cognitive disturbances associated with cerebral ageing and with neurodegenerative diseases.

The invention relates also to pharmaceutical compositions comprising the association between 4-{3-[cis-hexahydrocyclopenta[c]pyrrol-2(1H)-yl]propoxy}benzamide, or addition salts thereof with a pharmaceutically acceptable acid or base, and an acetylcholinesterase inhibitor in combination with one or more pharmaceutically acceptable excipients.

In the pharmaceutical compositions according to the invention, the proportion of active ingredients by weight (weight of active ingredients over the total weight of the composition) is preferably from 5 to 50%.

Among the pharmaceutical compositions according to the invention there will be more especially used those which are suitable for administration by the oral, parenteral and especially intravenous, per- or trans-cutaneous, nasal, rectal, perlingual, ocular or respiratory route, more specifically tablets, dragées, sublingual tablets, hard gelatin capsules, glossettes, capsules, lozenges, injectable preparations, aerosols, eye or nose drops, suppositories, creams, ointments, dermal gels etc.

Besides 4-{3-[cis-hexahydrocyclopenta[c]pyrrol-2(1H)-yl]propoxy}benzamide and the acetylcholinesterase inhibitor compound, the pharmaceutical compositions according to the invention comprise one or more excipients or carriers selected from diluents, lubricants, binders, disintegration agents, stabilisers, preservatives, absorbents, colourants, sweeteners, flavourings etc.

By Way of Non-Limiting Example there May be Mentioned:
- as diluents: lactose, dextrose, sucrose, mannitol, sorbitol, cellulose, glycerol,
- as lubricants: silica, talc, stearic acid and its magnesium and calcium salts, polyethylene glycol,
- as binders: magnesium aluminium silicate, starch, gelatin, tragacanth, methylcellulose, sodium carboxymethylcellulose and polyvinylpyrrolidone,
- as disintegrants: agar, alginic acid and its sodium salt, effervescent mixtures.

The compounds of the association may be administered simultaneously or sequentially. The administration route is preferably the oral route, and the corresponding pharmaceutical compositions may allow the instantaneous or delayed release of the active ingredients. The compounds of the association may moreover be administered in the form of two separate pharmaceutical compositions, each containing one of the active ingredients, or in the form of a single pharmaceutical composition, in which the active ingredients are in admixture.

Preference is given to the pharmaceutical compositions being tablets.

The useful dosage regimen varies according to the sex, age and weight of the patient, the administration route, the nature of the disorder and of any associated treatments and ranges from 0.5 mg to 100 mg of 4-{3-[cis-hexahydrocyclopenta[c]pyrrol-2(1H)-yl]propoxy}benzamide per 24 hours, more preferably 5 mg per day. The dose of the acetylcholinesterase inhibitor will be the same as or less than that used when it is administered on its own. In the case of donepezil, the dosage regimen is from 0.5 mg to 30 mg per day, preferred daily doses being 5 and 10 mg for the donepezil hydrochloride. For rivastigmine, the dosage regimen is from 1 mg to 20 mg per day. Preferred daily doses are 3 and 6 mg twice per day when rivastigmine is administered in the form of a tablet, whereas they are 4.6 mg and 9.5 mg per day when the product is presented in the form of a patch. In the case of galantamine, the dosage regimen is from 1 to 30 mg per day, preferred daily doses being 16 and 24 mg.

In preferred embodiments of the invention, the association between 4-{3-[cis-hexahydrocyclopenta[c]pyrrol-2(1H)-yl]propoxy}benzamide (compound S) and donepezil is administered at the following daily doses:

|  | Composition 1 | Composition 2 | Composition 3 |
|---|---|---|---|
| Hydrochloride of compound S (expressed as base) | 2 mg | 5 mg | 20 mg |
| Donepezil hydrochloride | 10 mg | 10 mg | 10 mg |

Pharmaceutical Composition:

Formula for the Preparation of 1000 Tablets each Containing 5 mg (Expressed as Base) of 4-{3-[cis-hexahydrocyclopenta[c]pyrrol-2(1H)-yl]propoxy}benzamide hydrochloride and 10 mg of donepezil hydrochloride:

4-{3-[cis-Hexahydrocyclopenta[c]pyrrol-2(1H)-yl]propoxy}benzamide
hydrochloride (expressed as base) . . . 5 g
Donepezil hydrochloride . . . 10 g
Maize starch . . . 20 g
Maltodextrin . . . 7.5 g
Colloidal silica . . . 0.2 g
Sodium starch glycolate . . . 3 g
Magnesium stearate . . . 1 g
Lactose . . . 55 g

BRIEF DESCRIPTION OF THE DRAWINGS

FIG. 1 shows the experimental procedure for the contextual serial discrimination test,
FIGS. 2-5 show the results obtained using the contextual serial discrimination test.

EXAMPLE A

Experiment in a Model of Episodic Memory, the Contextual Serial Discrimination Test The effects of 4-{3-[cis-hexahydrocyclopenta[c]pyrrol-2(1H)-yl]propoxy}benzamide and donepezil (both in the form of a hydrochloride), administered on their own or in combination, were studied using a contextual serial discrimination test in the middle-aged (14-15 months old) C57B16 mouse (n=12 per group) (Célérier et al., *Learn Mem.*, 2004, 11(2), 196-204; Tronche et al., *Behav. Brain Res.*, 2010, 215(2): 255-60). In this model, the middle-aged mice have a specific dysfunction of contextual memory compared to young mice, without a deficiency in spatial memory. This model is relevant for evaluating the effects of products in Alzheimer's disease because patients suffering from that form of dementia also have disturbances of contextual episodic memory, this being the case from a very early stage (Gold and Budson, *Expert Rev Neurother.*, 2008, 8(12): 1879-1891).

The mice, placed in a box with raised edges, learn two types of consecutive spatial discrimination (D1: white floor, then D2: black floor) on a floor with four holes, in which just one of the holes is baited, the arrangement being opposite in D1 and in D2 (see FIG. 1). Each discrimination is performed on a specific floor (black or white), which constitutes the internal context specific to each discrimination. 24 hours after the learning step, the mice are returned to the white contextual floor, and the following are measured:
- the percentage of correct responses (i.e. % of lowering the head into the hole that was baited during the learning exercise on the white floor),
- the percentage of interfering responses (i.e. % of lowering the head into the hole that was baited during the learning exercise on the black floor, the last context presented to the mice), and the percentage of errors (i.e. % of lowering the head into the two holes that were not baited during learning, whether on the white floor or on the black floor (see FIG. 1).

The results show that the middle-aged mice treated with the carrier have a percentage of correct responses which is close to the level of chance in this test on 4-hole boards (≈25%). Following chronic treatment for 9 days with donepezil hydrochloride (0.1 mg/kg of base per os), no significant improvement in the percentage of correct responses is observed compared to the carrier (see FIG. 2). In contrast, the level of correct responses increases by more than 60% compared to the carrier following chronic treatment for 9 days with 4-{3-[cis-hexahydrocyclopenta[c]pyrrol-2(1H)-yl]propoxy}benzamide hydrochloride at doses of 0.3 and 1 mg/kg of base per os (compound referred to as "S" in FIG. 2). Finally, administration of the association of 4-{3-[cis-hexahydrocyclopenta[c]pyrrol-2(1H)-yl]propoxy}benzamide (0.3 and 1 mg/kg of base per os) with donepezil (0.1 mg/kg of base per os) results in an increase in the level of correct responses of more than 100% compared to the carrier on its own. These results show clear potentiation of the effects of donepezil in the presence of 4-{3-[cis-hexahydrocyclopenta[c]pyrrol-2 (1H)-yl]propoxy}benzamide.

A very good correlation was moreover observed between the increase in the level of correct responses and the reduction in the level of interfering responses, thereby confirming the specific effect of each compound and of their association on contextual memory. Accordingly, the administration of the association of 4-{3-[cis-hexahydrocyclopenta[c]pyrrol-2 (1H)-yl]propoxy}-benzamide (0.3 and 1 mg/kg of base per os) with donepezil (0.1 mg/kg of base per os) significantly increases the power of contextual memory (correct responses−interfering responses) compared to that observed with the compounds on their own. This increase that is observed for the association cannot be explained by simply adding together the effects of the compounds administered on their own and shows synergistic activity of the two compounds when they are co-administered (see FIG. 3).

The results clearly demonstrate that the administration of these two compounds in association makes it possible to obtain a large synergistic effect which was entirely unexpected. Pharmacokinetic analyses have moreover shown that there was no pharmacokinetic-type interaction between the two treatments which might justify or interfere with the synergistic effect described above.

EXAMPLE B

Experiment with Rivastigmine in the Same Contextual Serial Discrimination Test

The effects of 4-{3-[cis-hexahydrocyclopenta[c]pyrrol-2 (1H)-yl]propoxy}benzamide and rivastigmine (used in the form of a hydrogen tartrate), administered on their own or in combination, were studied using the contextual serial discrimination test in the middle-aged C57B16 mouse described in the Example above.

In this model it has been shown that, compared to young mice, the middle-aged mice have a contextual memory deficit due to the fact that the last context in which they learnt the location of the baited hole (i.e. the black floor) substantially interferes with memory of the baited hole in the first context presented during learning (i.e. the white floor). Because of this fact, the elderly mice have negative values for the power of contextual memory (correct responses−interfering responses) because the percentage of interfering responses is higher than the percentage of correct responses. In contrast, the young mice have a positive power of contextual memory (Tronche et al., *Behav. Brain Res.,* 2010, 215(2): 255-60).

As in the Example above, the results of this study confirm the contextual memory deficit in middle-aged mice, the mice treated with the carrier showing a negative contextual memory power of −28% (see FIG. 4). Following chronic treatment for 9 days with rivastigmine at a dose of 0.1 mg/kg of base per os, a slight increase in the power of contextual memory compared to the carrier is observed (−9% versus −28%), but it still remains negative, the percentage of interfering responses still being greater than the percentage of correct responses, giving rise to the conclusion that the 0.1 mg/kg dose of rivastigmine is a sub-active dose.

Similarly, the power of contextual memory increases only slightly compared to the carrier following chronic treatment for 9 days with 4-{3-[cis-hexahydrocyclopenta[c]pyrrol-2 (1H)-yl]propoxy}benzamide hydrochloride at doses of 0.3 and 1 mg/kg of base per os (+6% and +10%, respectively, versus −28%). In contrast, administration of the association of rivastigmine (sub-active dose of 0.1 mg/kg of base per os) with 4-{3-[cis-hexahydrocyclopenta[c]pyrrol-2(1H)-yl]propoxy}benzamide (0.3 or 1 mg/kg of base per os) results in a substantial increase in the power of contextual memory, which then becomes significantly superior (% of correct responses >% of interfering responses), on the one hand relative to the value obtained with the carrier and on the other hand relative to that obtained for rivastigmine on its own (+28% and +28% versus −9%, respectively). These results show clear potentiation of the effects of rivastigmine at a sub-active dose in the presence of active doses of 4-{3-[cis-hexahydrocyclopenta[c]pyrrol-2(1H)-yl]propoxy}benzamide, which is reflected by an increase in the memory performance of the mice treated with the association.

In this second example too, the increase in the power of contextual memory observed for the two associations cannot be explained by simply adding together the effects of the compounds administered on their own and shows entirely unexpected synergistic activity for the two compounds when they are co-administered.

Pharmacokinetic analyses have moreover shown that there was no pharmacokinetic-type interaction between the two treatments which might justify or interfere with the synergistic effect described above.

In conclusion, the results presented above demonstrate synergistic activity between 4-{3-[cis-hexahydrocyclopenta [c]pyrrol-2(1H)-yl]propoxy}benzamide and rivastigmine in terms of cognitive performance, this being the case without any pharmacokinetic interaction.

EXAMPLE C

Experiment with Galantamine in the Same Contextual Serial Discrimination Test

The effects of 4-{3-[cis-hexahydrocyclopenta[c]pyrrol-2 (1H)-yl]propoxy}benzamide and galantamine (used in the form of a hydrobromide), administered on their own or in combination, were also studied using the contextual serial discrimination test in the middle-aged C57B16 mouse.

As in the Examples above, the results of this study confirm the contextual memory deficit of middle-aged mice, the mice treated with the carrier showing a negative contextual memory power of −28% (see FIG. 5).

Following chronic treatment for 9 days with galantamine at a dose of 0.3 mg/kg of base per os, there is observed no significant improvement in the power of contextual memory compared to the carrier (−18% versus −28%), the power remaining markedly negative (% interfering responses >% correct responses); the 0.3 mg/kg dose of galantamine is therefore sub-active. Neither, after chronic treatment for 9 days with 4-{3-[cis-hexahydrocyclopenta[c]pyrrol-2(1H)-yl]propoxy}benzamide hydrochloride at a dose of 0.3 mg/kg of base per os, does contextual memory power increase significantly compared to the carrier (−3% versus −28%, respectively). Moreover, after chronic treatment for 9 days with 4-{3-[cis-hexahydrocyclopenta[c]pyrrol-2(1H)-yl]propoxy}benzamide hydrochloride at a dose of 1 mg/kg of base per os, it increases only slightly compared to the carrier (+9% versus −28%). In contrast, administration of the association of 4-{3-[cis-hexahydrocyclopenta[c]pyrrol-2(1H)-yl]propoxy}benzamide (0.3 and 1 mg/kg of base per os) with galantamine (sub-active dose of 0.3 mg/kg of base per os) results in a substantial increase in contextual memory power, which becomes significantly superior compared to the value obtained with the carrier on its own (+31% and +24% versus −28%, respectively). These results show clear potentiation of the effects of galantamine at a sub-active dose in the presence of a sub-active or slightly active dose of 4-{3-[cis-hexahydrocyclopenta[c]pyrrol-2(1H)-yl]propoxy}benzamide, which is reflected by an increase in the memory performance of the mice treated with the association.

Here too, in this third Example of association with an acetylcholinesterase inhibitor, the increase in the power of contextual memory observed cannot be explained by simply adding together the effects of the compounds administered on their own.

In conclusion, the results presented above show synergistic activity between 4-{3-[cis-hexahydrocyclopenta[c]pyrrol-2(1H)-yl]propoxy}benzamide and galantamine in terms of cognitive performance.

EXAMPLE D

Irwin's Primary Observation Test

The effects, in terms of safety, of 4-{3-[cis-hexahydrocyclopenta[c]pyrrol-2(1H)-yl]propoxy}-benzamide and donepezil (both in the form of a hydrochloride), administered on their own or in association, were studied using Irwin's primary observation test in the C57B16 mouse (n=4 individuals per group).

Behavioural changes, physiological and neurotoxic symptoms, rectal temperature and pupil diameter were recorded using a standardised observation grid derived from that of Irwin.

It was observed that 4-{3-[cis-hexahydrocyclopenta[c]pyrrol-2(1H)-yl]propoxy}benzamide (0.3 and 1 mg/kg of base per os) and donepezil (0.1 and 0.3 mg/kg of base per os), administered on their own or in co-administration, brought about no observable changes in Irwin's test in the mouse. At the strongest dose (1 mg/kg of base per os), donepezil administered on its own reduces reactivity to touch and causes slight sedation. No potentiation of the adverse effects of donepezil at 1 mg/kg is observed when it is co-administered with 4-{3-[cis-hexahydrocyclopenta[c]pyrrol-2(1H)-yl]propoxy}benzamide (0.3 and 1 mg/kg of base per os). On the contrary, when 4-{3-[cis-hexahydrocyclopenta[c]pyrrol-2(1H)-yl]propoxy}benzamide at the strongest dose (1 mg/kg of base per os) is co-administered with donepezil at 1 mg/kg p.o., no sedation is observed, which suggests that 4-{3-[cis-hexahydrocyclopenta[c]pyrrol-2(1H)-yl]propoxy}benzamide antagonises the sedation caused by donepezil at 1 mg/kg p.o.

In conclusion, the results presented above demonstrate synergistic activity between 4-{3-[cis-hexahydrocyclopenta[c]pyrrol-2(1H)-yl]propoxy}benzamide and donepezil in terms of cognitive performance, this being the case with a good safety profile and without pharmacokinetic interaction.

The invention claimed is:

1. A composition comprising a combination of 1-20 mg of 4-{3-[cis-hexahydrocyclopenta[c]pyrrol-2(1H)-yl]propoxy}benzamide of formula (I):

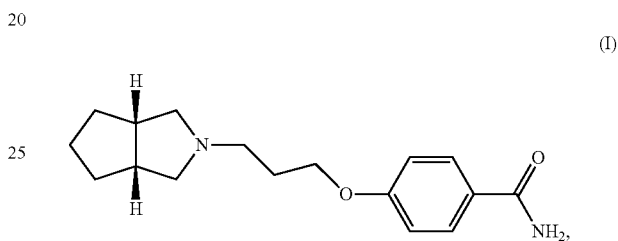

or an addition salt thereof with a pharmaceutically acceptable acid or base, and 3-20 mg of an acetylcholinesterase inhibitor.

2. The composition of claim 1, wherein the 4-{3-[cis-hexahydrocyclopenta[c]pyrrol-2(1H)-yl]propoxy}benzamide is in the form of an oxalate or hydrochloride.

3. The composition of claim 1, wherein the acetylcholinesterase inhibitor is donepezil, rivastigmine or galantamine.

4. The composition of claim 1, wherein the acetylcholinesterase inhibitor is donepezil hydrochloride, rivastigmine hydrogen tartrate or galantamine hydrobromide.

5. The composition of claim 1, wherein the 4-{3-[cis-hexahydrocyclopenta[c]pyrrol-2(1H)-yl]propoxy}benzamide is in the form of a hydrochloride which is present at a dose of 2 mg, 5 mg or 20 mg (expressed as base), and wherein the acetylcholinesterase inhibitor is donepezil hydrochloride which is present at a dose of 10 mg.

6. A pharmaceutical composition comprising as active ingredient the composition of claim 1, in combination with one or more pharmaceutically acceptable excipients.

7. The pharmaceutical composition of claim 6, wherein the 4-{3-[cis-hexahydrocyclopenta[c]pyrrol-2(1H)-yl]propoxy}benzamide is in the form of a hydrochloride which is present at a dose of 2 mg, 5 mg or 20 mg (expressed as base), and wherein the acetylcholinesterase inhibitor is donepezil hydrochloride which is present at a dose of 10 mg.

* * * * *